United States Patent [19]

Whitaker, Jr.

[11] Patent Number: 4,714,759

[45] Date of Patent: Dec. 22, 1987

[54] IMMUNOTOXIN THERAPY OF ALLERGY

[76] Inventor: Robert B. Whitaker, Jr., R.R. 1, Box 936, Turner, Me. 04282

[21] Appl. No.: 803,230

[22] Filed: Dec. 2, 1985

[51] Int. Cl.⁴ ...................... C07K 17/00; C07K 15/00
[52] U.S. Cl. .................................... 530/391; 530/405; 530/389; 530/403; 530/404; 530/402; 530/390; 424/88; 424/92; 424/91; 514/885; 514/829; 514/389
[58] Field of Search ............................. 424/88, 92, 91; 530/391, 405; 514/885, 829, 389

[56] References Cited

U.S. PATENT DOCUMENTS 4,564,600 1/1986 Ali .......................................... 424/88
4,661,347 4/1987 Muller .................................... 424/85

OTHER PUBLICATIONS

Killen et al, *J. Immunol.*, 133, 1984, pp. 2549–2553.
Jansen et al, *Immunological Rev.*, 62, 1982, pp. 185–216.
Vitetta et al, *Immunol. Rev.*, 62, 1982, pp. 159–183.
Vallera et al, *J. Exp. Med.*, 155, 1982, pp. 949–954.
Farkas et al, *Immunol.*, 45, 1982, pp. 483–492.
Masuho et al, *J. Biochem*, 91, 1982, pp. 1583–1591.
Ramakrishnon et al, *Cancer Res.*, 44, 1984, pp. 201–208.

*Primary Examiner*—John Kight
*Assistant Examiner*—Garnette D. Draper
*Attorney, Agent, or Firm*—Wolf, Greenfield & Sacks

[57] ABSTRACT

A product and process for treating allergy are described. An immunotoxin specific for the IgE isotype is used to eliminate the IgE producing B-lymphocytes responsible for allergy.

22 Claims, No Drawings

IMMUNOTOXIN THERAPY OF ALLERGY

This invention relates generally to immunotoxins and more particularly to immunotoxin therapy of allergy.

Allergy is a hypersensitive state induced by an exaggerated immune response to a foreign agent. The body's allergic reaction to the foreign agent can range from minor inflammation and discomfort to death. Allergy affects the lives of millions, often dictating what people can eat, touch and smell and even where people can live.

Current treatment for allergy focuses on two approaches. One treats only the symptoms of allergy, utilizing drugs such as antihistamines. This approach often entails repeated doses and can involve undesirable side effects. Moreover, it acts only to treat symptoms, not the underlying condition responsible for the hypersensitive state. Another approach, desensitization therapy, involves injection with specific allergens. Patient-specific allergens must first be recognized. Then the patient is injected repeatedly with low doses of the allergens. This approach can involve discomfort and can require as many as 50 visits to a doctor. Moreover, the allergen to which the patient is hypersensitive cannot always be identified, making desensitization treatment impossible. Neither of the above approaches, in addition to the drawbacks already cited, can guarantee the elimination of the hypersensitive state. Likewise, neither can protect against the development of a hypersensitive state.

The IgE producing subclass of B-lymphocytes has been shown to play a critical role in the allergic response. An allergen stimulates the production and release of IgE by IgE producing B-lymphocytes. The IgE interacts with mast cells to cause the release of histamine. This release can ultimately result in the symptoms associated with allergy.

This invention, Immunotoxin Therapy of Allergy, operates by eliminating the IgE producing B-lymphocytes. Elimination of these lymphocytes causes the levels of IgE to fall to substantially zero making an allergic response substantially impossible. The selective elimination of IgE producing B-lymphocytes is possible since IgE is not required by the host for survival. Deletion of all IgE producing B-lymphocytes does not render a human or an animal immunologically defenseless since lymphocytes producing other classes of immunoglobulin are left intact.

Immunotoxins are antibodies (or hormones) or fragments of antibodies coupled to a toxin. The antibody retains its ability to recognize and bind to a specific antigen. If the antibody binds to a cell surface antigen, the toxin may be passed into the cytoplasm of the cell where it inactivates, incapacitates or destroys the cell.

Immunotoxin research has focused on developing immunotoxins for cancer therapy. Antibodies against tumor specific antigens are used to deliver a toxin to the tumor in situ. This immunotoxin tumor therapy involves recognizing non-self antigens and eliminating a population of cells considered aberrant.

SUMMARY OF THE INVENTION

It is an object of the invention to provide an improved treatment for allergy.

Another object of the invention is to provide a treatment for allergy that does not require identification of a specific allergen.

Another object of the invention is to provide a treatment for allergy that is not limited to affecting the hypersensitive response to a particular allergen.

Another object of the invention is to provide a treatment for allergy that affects the underlying cause of allergy rather than just treating symptoms.

Another object of the invention is to provide a treatment for allergy not requiring repeated doses.

Another object of the invention is to provide a treatment for allergy having reduced undesirable side effects.

Another object of the invention is to provide a treatment for allergy that is capable of being administered prior to detection of any of the symptoms of allergy.

According to the invention, a method for treating allergy is provided. An immunotoxin is introduced in vivo to selectively deplete the population of cells bearing the IgE isotype by killing or removing that population of cells. Removal is meant to include any means of causing the cell to discontinue making IgE immunoglobulin available to the body in response to an allergen. Also according to the invention an immunotoxin having activity selective for cells bearing the IgE isotype is provided. The immunotoxin binds only to those lymphocytes carrying the IgE isotype on the cell surface. IgE producing B-lymphocytes carry the IgE isotype on the cell surface. Once bound, the toxin gains entry to the cell cytoplasm. In the cytoplasm, the toxin molecule incapacitates the cell's biosynthetic machinery, thus precipitating cell death. Eliminating IgE producing B-lymphocytes eliminates the potential for an allergic response.

DETAILED DESCRIPTION OF THE PREFERRED EMBODIMENTS

The immunotoxin is an antibody or a fragment of an antibody coupled to a toxin. The antibody must selectively recognize IgE isotype, the antigenic site shared by immunoglobulins of the IgE class, but not present on all other classes of immunoglobulin. Goat anti-mouse IgE isotype has been used successfully in experiments on mouse hypersensitivity, although any antibody having the required specificity is all that is necessary, e.g., rat anti-mouse IgE, mouse anti-mouse IgE or rabbit anti-mouse IgE. Human anti-human IgE isotype would be most preferable for treating human hypersensitivity since there would be no immune response to this human antibody when administered.

The anti-IgE may be prepared and isolated according to well known techniques. Most preferably, the anti-IgE is a monoclonal antibody which allows for unlimited production and insures uniformity, both with respect to the binding specificity and affinity of the antibody and the coupling of the antibody to the toxin.

Toxin molecules found useful in the synthesis of immunotoxins are either plant or bacteria derived proteins. Generally, they consist of an A chain and a B chain, linked by a disulphide bond. The A chain can enzymatically inhibit protein synthesis and, when introduced to the cytoplasm of a cell, precipitates cell death. The B chain is believed to mediate the entry of the A chain into a cell.

An immunotoxin can be constructed by binding the intact toxin or only the A chain to the antibody. It is possible to separate the A chain and the B chain by cleaving the disulfide bond joining them. (See Vitetta et al, "Neoplastic B Cells as Targets for Antibody-Ricin A Chain Immunotoxins", *IMMUNOLOGICAL REV.*, Vol. 62, P. 159 [1982]). The A chain may then be purified and bound to the antibody. Since an antibody bound to a cell-surface immunoglobulin may be taken up into the cell's cytoplasm by endocytosis, the antibody may substitute for the B chain and mediate the entry of the A chain into the cell's cytoplasm. In this regard, Fab fragments can be more effective than whole antibody of $Fab_2$ fragments. The fab fragment is more readily endocytosed than whole antibody or $Fab_2$ fragments. Whole antibody or $Fab_2$ fragment binding to cell-surface antigens will crosslink with other bound whole antibody or $Fab_2$ fragments forming caps which are expelled from the surface of the cell. Fab fragments, unlike whole antibody or $Fab_2$ fragments, cannot crosslink and are therefore more likely to be taken, along with the bound toxin, into the cytoplasm by endocytosis.

It is also possible to bind the A chain to one antibody and the B chain to another antibody. An antibody-B chain bound to a cell enhances the uptake of the A chain. Where A chain is bound to antibody, it is important that the bond be strong enough to prevent dissociation of the immunotoxin in vivo since free A chain tends to accumulate in the liver and kidney where it can cause serious damage.

Where the intact toxin molecule is used to construct the immunotoxin, preferably the B chain portion is bound to the antibody so that the A chain is left intact. The strong natural forces holding the A and B chains together limit the dangerous release of free A chain. Furthermore, the B chain is then present to facilitate A chain entry into the cell's cytoplasm.

The antibody or antibody fragment and the toxin are covalently linked to form a hybrid molecule, the immunotoxin. The linkage can be accomplished by any chemical reaction that will bind the two molecules so long as the antibody molecule retains its specificity and the toxin molecule its toxicity. Periodate-carbohydrate and thioether reactions are among those that can be used successfully and are described in the literature. (See Killen and Lindstrom 1984, "Specific killing of lymphocytes that cause experimental Autoimmune Myesthenia Gravis by toxin-acethylcholine receptor conjugates." *Jour. Immun.* 133:2549–2553; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". *Immunological Reviews* 62:185–216; and Vitetta et al, supra.

In the murine system, binding the A chain of ricin to a Fab fragment has produced an effective immunotoxin. A superior immunotoxin was achieved by binding whole antibody via a sulfo-SADP reaction to pokeweed antiviral protein.

The immunotoxin is then delivered into the bloodstream, preferably by an intravenous injection. The immunotoxin selectively binds to cells bearing IgE. Once bound, the toxin is introduced into the cytoplasm where it eventually causes cell death. The IgE producing population of cells responsible for hypersensitivity are eliminated. The hypersensitive response which depends upon production of IgE is likewise eliminated.

EXAMPLE 1

Materials and Reagents

C57B1/6 ×DBA/2 $F_1$ mice (BDF1) were obtained from the Charles River Breeding Labs., Wilmington, MA, and maintained in the Bates Animal Facility with access to food and water ad libitum. Female mice aged 6–8 weeks were used in all experiments. Goat anti-mouse IgE antiserum was obtained from Miles-Yeda (Naperville, IL). Pokeweed antiviral protein (PAP) was obtained from Cooper Biomedical (Malvern, PA) and stored refrigerated until use in phosphate buffered saline as supplied. Pierce Chemical Co. (Rockford, IL) supplied the heterobifunctional crosslinking agent Sulfo-SADP. Unless otherwise specified, all other chemicals were obtained from Sigma Chemical Co., St. Louis, MO.

Preparation of PAP-Goat anti-mouse IgE Immunotoxin (IT) by a Sulfo-SADP Coupling Reaction.

Goat anti-mouse IgE antisera was processed with 50% saturated ammonium sulfate to yield an immunoglobulin-enriched fraction that was extensively dialyzed prior to use. One milligram of this material was reacted with 15.15 micrograms of sulfo-SADP by stirring at 4° C. in a total volume of 1.074 ml phosphate-buffered saline, pH 7.2 (PBS). One milligram of PAP in 1 ml PBS was added to this mixture with stirring. Until this point, all manipulations had been carried out either under safe-light conditions or in the dark. The antibody-SADP-PAP mixture was then irradiated with visible light for ten minutes while being stirred in an ice bath. The resultant material was then dialyzed against PBS and tested for immunotoxin activity. This IT is calculated to have five molecules of PAP per immunoglobulin molecule.

In vivo assessment of IT

High IgE producing BDF1 mice were immunized i.p. with 0.1 micrograms of ovalbumin (OVA) absorbed to 1 milligram alum in a total volume of 0.5 ml PBS. Mice were immediately treated intravenously with either 100 micrograms of IT or 100 micrograms of the immunoglobulin (IG) used to prepare the IT to assay activity and specificity of the PAP immunotoxin. Fourteen days after immunization, mice were bled for 0.25 ml by cardiac puncture, the blood pooled by treatment group, and allowed to clot at room temperature. The clarified serum was titered for anti-OVA IgE using a passive cutaneous anaphylaxis assay. The backs of Sprague-Dawley rats were shaved twenty-four hours prior to use and divided into quadrants for injection. Mouse serum dilutions in PBS were injected in 0.05 ml volumes subcutaneously. Twenty-four hours after sensitization, the rats were challenged by intracardiac injection of one ml PBS containing 5 mg OVA and 1% Evan's blue dye. Anaphylactic reactions were assessed thirty minutes later by examining the interior surface of the skin. A bluing diameter of greater than 10 mm indicated a positive reaction.

IgG anti-OVA titers were determined using a standard enzyme-linked immunosorbent assay protocol. Buchanan, Kamack & Ruddle, *J. Immunol. Methods,* 42 (2): 179–185, 1981; Avrameas; *Immunochemistry,* Vol 6, pp 43–52, 1969; SIGMA(®) Chemical Company product bulletin P5521, Type VII-S, 1981. The enzyme-antibody conjugate used in the assay was alkaline phosphatase (SIGMA ®, Catalogue # P5521, Type VII-S) coupled to goat anti-mouse IgG antibody (SIGMA(®) Catalogue #M3014).

In vivo results

Table I provides the results for the in vivo test of activity for IT and IG. The titers indicate that a single treatment with 100 ug of IT was sufficient to reduce the anti-OVA IgE titer by 800-fold. In contrast, IG treatment of the BDF1 mice had no effect on the titer of anti-OVA IgE class antibody. IT treatment did not inhibit the entire antibody-producing population. The PAP contained in the IT preparation had no effect on the B lymphocyte population in general.

TABLE I

IN VIVO ACTIVITY OF IT AND IG

| | IgE TITERS | | | | | |
|---|---|---|---|---|---|---|
| | Undilute | 1/50 | 1/100 | 1/200 | 1/400 | 1/800 |
| CONTROL | → | → | → | → | → | →+ |
| IT | + | | | | | |
| IG | → | → | → | → | →+ | +/− |

| | IgG TITERS | | | | | |
|---|---|---|---|---|---|---|
| | Undil. | ↓ | ↓ | ↓ | 1/16 | 1/32 | 1/64 |
| CONTROL | + | | | | | | |
| IT | → | → | → | → | → | →+ | |
| IG | → | → | → | → | → | → | →+ |

The results demonstrate that IT treatment is an effective means for the reduction of IgE titers in BDF1 mice immunized for the development of IgE antibody.

Example 2

An immunotoxin directed against IgE secreting B cells was prepared by conjugating the toxic subunit of the two chain protein ricin and the Fab' fragment of goat anti-mouse IgE antibody. Mice immunized to produce high titers of anti-ovalbumin IgE antibody were subsequently treated with this immunotoxin in an attempt to selectively destroy the B cells that express cell surface IgE.

Mice

Male (Exp. 4) and Female (Exp. 1,2,3,5) C57B1/6 mice were purchased from Jackson Laboratory, Bar Harbour, ME.

Preparation of the antibody-ricin A chain conjugate by a MBS coupling reaction The A chain of Ricinus communis agglutinin (Calbiochem-Behring Corp., LaJolla, CA) was separated from the B chain by reducing the disulfide bond that holds the two chains together. This reduction was accomplished by adding .25 ml of 2-mercaptoethanol to intact ricin (5 mg in 5 ml PBS) and incubating for 2 hours at room temperature while stirring. The A chain was isolated employing affinity chromatography. The solution containing the separated chains was run over a sepharose-4B column, which bound and retained the B chains. The effluent, containing only the A chains, was concentrated to 2.5 ml (approx. 2.5 mg. protein) by vacuum dialysis against 20 mM PBS, pH 7.4, containing 0.05% 2-mercaptoethanol. Dimethylformamide (13 ul), containing 32 ug MBS was added to the concentrate and incubated at room temperature for 30 minutes. This mixture (400 ul) was then incubated for 2 hours with goat anti-mouse antibody Fab monovalent fragments that had been prepared as follows: Goat anti-mouse IgE from Miles-Yeda (0.6 ml of a 1 mg/ml solution) was mixed with 30 ul of dithiothreitol and was incubated at room temperature for 30 minutes. This mixture was run over a sephadex G-50 column, pH 7.4, and the peak 3 ml were collected.

Immunizations

To induce the production of anti-ovalbumin IgE antibodies, mice were injected i.p. with 0.2 ug ovalbumin in 1 mg of aluminum hydroxide gel (alum) which had been prepared according to the method of Revoltella and Ovary (1969). *Int. Arch. Allergy Appl. Immunol.* 36, 283.

The immunotoxin (0.2 ml of a 1:10 dilution of stock) or anti-IgE 0.02 mg in 0.2 ml PBS) was injected i.v. 1 day after immunizing for IgE production. The exception to this was experiment 5, in which the anti-IgE treatment was performed 5 days after immunizing for IgE production. Sera from the treated mice was collected 2 weeks later and was tested for anti-ovalbumin IgE activity.

Passive cutaneous anaphylaxis for detection of IgE

Anti-ovalbumin IgE titers in the mouse sera were determined by Passive Cutaneous Anaphalaxis (PCA) according to the method of Braga and Mota, 1976. "Homologous Passive Cutaneous Anaphalaxis (PCA) in mice and heterlogous PCA induced in rats with mouse IgE.", *Immunology*, 30, 655. The PCA titer of the sera was defined as the reciprocal of the highest dilution which gave a reaction of 5 mm mean diameter on the everted skin surface of the sensitized rat.

TABLE II

| | IgE Titer | | |
|---|---|---|---|
| | Control | Immunotoxin Treated | Anti-IgE Treated |
| Exp. 1 | >320 | N.D. | N.D. |
| Exp. 2 | >320 | 10 | N.D. |
| Exp. 3 | >320 | 40 | 160 |
| Exp. 4 | >320 | 80 | 40 |
| Exp. 5 | >320 | 80 | 0 |

Induction of an anti-ovalbumin IgE response

Each of three mice were immunized for IgE production, as described in Immunizations. On day 4, the mice were bled and their sera were collected and pooled. A PCA was then performed to determine the IgE titer of the sera. As indicated in Exp. 1 of Table 2, a positive reaction was observed at a titer of >320.

Suppression of the IgE response with the prepared immunotoxin.

Six mice were immunized for IgE production as in Experiment 1, with three to be used as a control (no further treatment) and three to be treated with the immunotoxin. On day 14, each of the groups was bled, their sera were collected, and a PCA was performed to compare IgE titers. As indicated in exp. 2 of Table 2. the IgE titer was >320 for the control group and was 10 for the group treated with the immunotoxin. The immunotoxin reduced the titer of IgE, by selectively destroying IgE producing B-lymphocytes.

Suppression of the IgE response with the prepared immunotoxin and anti-IgE

Experiments 3 and 4 were performed exactly as Experiment 2, with the following added control: Three mice were treated i.v. on day 1 with 20 ug of anti-IgE in 0.2 ml PBS. The IgE titers were determined as before.

In Exp. 3, the IgE titer was >320 for the untreated control, 40 for the group treated with immunotoxin, and 160 for the group treated with anti-IgE. In Exp. 4, the IgE titer was >320 for the untreated control group, 80 for the group treated with the immunotoxin, and 40 for the group treated with anti-IgE. The immunotoxin again reduced the titer of IgE, by selectively destroying IgE producing B-lymphocytes.

Experiment 5 was identical to experiments 3 and 4, only the anti-IgE treatment was performed on day 5 instead of day 1. Whereas the IgE titers for the untreated control group and the immunotoxin treated group were the same as in experiment 4 (>320 and 890, respectively), the titer for the anti-IgE treated group was 0.

The immunotoxin contained an Fab fragment of the antibody while the anti-IgE control used the intact antibody. Fab fragments contain only one binding site and therefore will not clear antigen from solution. Intact antibody with two sites will clear antigen, in this case IgE. It was expected that the anti-IgE would clear the IgE from the serum and thus depress the anti-OVA titers. The amount of anti-IgE employed (20 ug) was at least four times the amount of immunoglobulin present in the immunotoxin.

In Exp. 5, since treatment was delayed until 5 days after immunization, the IgE anti-OVA response was well underway, the mice were 'allergic' at the time of treatment. The immunotoxin once again reduced the titer of IgE by selectively destroying IgE producing B-lymphocytes. Treatment with anti-IgE gave the expected result of no detectable IgE. Since this treatment with a clearing antibody was closer to the time of serum assay, this result is expected if the antiserum is indeed directed against mouse IgE. Thus the anti-IgE control treatment demonstrates that the antibody used in the immunotoxin was directed against mouse IgE.

The methods and immunotoxins of this invention are useful in mammals having IgE and subject to allergic reactions. The methods and materials of this invention thus can be used in connection with man and animals.

The exact amounts of immunotoxins to be administered will very greatly depending upon species and body weight of the individuals being treated. In all cases, the immunotoxin used is used below a level which causes general malaise in the body to which it is applied. Application can be subcutaneous, intramuscular or intravenous. In some cases oral ingestion is possible. In the preferred embodiment, the immunotoxins are administered to the body intravenously in physiologically compatible fluids such as saline and a physiological pH as for example, 7.2 to 7.4.

While the above examples illustrate the incapacitation or destruction of IgE producing cells in animals, the immunotoxin reactions of this invention are useful in man to alleviate allergy symptoms.

The specific dosage levels can vary greatly depending upon the specific species and body weights of individuals treated. Work to date has shown that in animals, a single intravenous injection of an immunotoxin carrying approximately 1/20 the 10 day lethal dose of pure ricin A chain is effective to inhibit a lymphocyte subpopulation. Such doses have also been reported in the literature. Jansen, F. K., H. E. Blythman, D. Carriere, P. Casellas, O. Gros, P. Gros, J. C. Laurent, F. Paolucci, B. Pau, P. Poncelet, G. Richer, H. Vidal, and G. A. Voisin. 1982. Immunotoxins: Hybrid molecules combining high specificity and potent cytotoxicity. *Immunological Reviews* 62:185-216. Vitteta, E. S., K. A. Krolick, and J. W. Uhr, 1982. "Neoplastic B cells as Targets for Antibody-Ricin A Chain Immunotoxins", *Immunological Reviews* 62:159-184. Jansen estimates that for human tumor therapy, doses of an immunotoxin carrying approximately 1/10 the 10 day lethal dose of pure ricin A chain are effective. For Immunotoxin Therapy of Allergy in humans, the preferred dose would be an immunotoxin carrying approximately 1/20 to 1/10 the 10 day lethal dose for pure ricin A chain, or about 0.05 to 10 milligrams per day The PAP-carrying immunotoxin prepared according to Example 1 is at least as effective as ricin-carrying immunotoxin. Thus, the preferred dose of PAP-carrying immunotoxin for Immunotoxin Therapy of Allergy in Humans would fall in the same range, about 0.05 to 10 milligrams per day.

It should be understood that various changes and modifications of the preferred embodiments may be made within the scope of this invention. Thus it is intended that all matter contained in the above description shall be interpreted in an illustrative and not limited sense.

What I claim is:

1. A method for treating allergy comprising, introducing in vivo an immunotoxin to selectively deplete the population of cells bearing the IgE isotype.

2. A method for treating allergy as claimed in claim 1 wherein said immunotoxin is an antibody coupled to a toxin, said antibody having specificity for IgE isotype.

3. A method for treating allergy as claimed in claim 2 wherein said toxin is A chain.

4. A method for treating allergy as claimed in claim 3 wherein said A chain is coupled to said antibody via a MBS coupling reaction.

5. A method for treating allergy as claimed in claim 2 wherein said toxin is pokeweed antiviral protein.

6. A method for treating allergy as claimed in claim 5 wherein said pokeweed antiviral protein is coupled to said antibody via a SADP coupling reaction.

7. A method for treating allergy as claimed in claim 2 wherein said toxin is intact ricin having a B chain and an A chain.

8. A method for treating allergy as claimed in claim 7 wherein said B chain of said ricin is coupled to said antibody via a preiodate-carbohydrate coupling reaction.

9. A method for treating allergy as claimed in claim 1 wherein said immunotoxin comprises a mixture of
   a first immunotoxin comprising a first antibody having selective specificity for IgE isotype and coupled to A chain and,
   a second immunotoxin comprising a second antibody having selective specificity for IgE isotype coupled to B chain.

10. A method for treating allergy as claimed in claim 1 wherein said immunotoxin is a Fab fragment of an antibody coupled to a toxin, said Fab fragment having selective specificity for IgE isotype.

11. A method for treating allergy as claimed in claim 10 wherein said toxin is A chain.

12. A method for treating allergy as claimed in claim 11 wherein said A chain is coupled to said Fab fragment via a MBS coupling reaction.

13. A method for treating allergy as claimed in claim 1 wherein said immunotoxin is a $Fab_2$ fragment of antibody coupled to a toxin, said $Fab_2$ fragment having selective specificity for IgE isotype.

14. A preparation useful in treating allergy consisting essentially of immunotoxin having activity selective for cells bearing the IgE isotype.

15. A preparation as claimed in claim 14 wherein said immunotoxin consists essentially of antibody coupled to toxin, said antibody having selective specificity for IgE isotype.

16. A preparation as claimed in claim 14 wherein said immunotoxin consists essentially of $Fab_2$ fragment of antibody coupled to toxin, said $Fab_2$ fragment having selective specificity for IgE isotype.

17. A preparation as claimed in claim 14 wherein said immunotoxin consists essentially of Fab fragment coupled to toxin, said Fab fragment having selective specificity for IgE isotype.

18. A preparation as claimed in claim 17 wherein said toxin is A chain.

19. A preparation as claimed in claim 18 wherein said A chain is coupled to said Fab fragment via a MBS coupling reaction.

20. A preparation as claimed in claim 15 wherein said antibody is a monoclonal antibody.

21. A preparation as claimed in claim 17 wherein said toxin is pokeweed antiviral protein..

22. A preparation as claimed in claim 21 wherein said toxin is bound to said Fab fragment via a SADP coupling reaction.

* * * * *